United States Patent [19]

Heindel et al.

[11] Patent Number: 5,356,929
[45] Date of Patent: Oct. 18, 1994

[54] REDUCED AND QUATERNIZED PSORALENS AS PHOTO-ACTIVATED THERAPEUTICS

[75] Inventors: Ned D. Heindel, Easton, Pa.; Jeffrey D. Laskin, Piscataway, N.J.

[73] Assignee: Lehigh University, Bethlehem, Pa.

[21] Appl. No.: 52,660

[22] Filed: Apr. 23, 1993

Related U.S. Application Data

[63] Continuation-in-part of Ser. No. 633,268, Dec. 21, 1990, Pat. No. 5,216,176, which is a continuation-in-part of Ser. No. 300,869, Jan. 23, 1989, abandoned.

[51] Int. Cl.$^5$ .......................................... C07D 307/77
[52] U.S. Cl. ..................................... 514/455; 549/209; 549/387
[58] Field of Search ................. 549/387, 209; 514/455

[56] References Cited

U.S. PATENT DOCUMENTS

| | | | |
|---|---|---|---|
| 4,124,598 | 11/1978 | Hearst et al. | 260/343.21 |
| 4,130,568 | 12/1978 | Confalone et al. | 260/343.21 |
| 4,151,291 | 4/1979 | Vallet | 424/281 |
| 4,294,822 | 10/1981 | Kaufman | 424/59 |
| 4,312,883 | 1/1982 | Baccichetti et al. | 424/279 |
| 4,452,811 | 6/1984 | della Valle | 424/281 |
| 4,727,517 | 4/1988 | della Valle et al. | 514/457 |
| 4,950,770 | 8/1990 | Heindel et al. | 549/282 |

OTHER PUBLICATIONS

"Coumarins From Brosimum Gaudichaudii"; by Wagner Viegas et al.; Journal of Natural Products, vol. 56, Mar. 1993; pp. 416–417.
Extracorporeal Photopheresis in the Treatment of AIDS-Related Complex: A Pilot Study by Emil Bisaccia et al.; American College of Physicians 1990; pp. 270–275.
"Syntheses of Psoralen Analogues & Evaluation of Their Inhibition of Epidermal Growth Factor Binding"; by Ned Heindel et al.; Journal of Pharmaceutical Sciences vol. 80, No. 7, Jul. 1991; pp. 686–689.
"Treatment of Autoimmune Disease with Extracorporeal Photochemotherapy: Progressive Systemic Sclerosis"; by Alain Rook et al.; The Yale Journal of Biology and Medicine 62 (1989) pp. 639–645.
"Treatment of Autoimmune Disease with Extracorporeal Photochemotherapy: Pemphigus Vulgaris-Preliminary Report"; by Alain Rook et al.; The Yale Journal of Biology & Medicine 62 (1989) pp. 647–652.
"Photopheresis Therapy of Cutaneous T-Cell Lymphoma: The Yale-New Haven Hospital Experience"; by Peter Heald et al.; The Yale Journal of Biology & Medicine 62 (1989), pp. 629–638.
"Experimental Murine & Primate Models for Dissection of the Immunosuppressive Potential of Photochemotherapy in Autoimmune Disease & Transplantation"; by C. Berger; The Yale Journal of Biology & Medicine 62 (1989), pp. 611–620.
"Chemical Research in Toxicology"; by John Hearst; Chem. Res. Toxicol, vol. 2., Mar./Apr. 1989 pp. 69–75.
"Light-Activated Drugs"; by R. Edelson; Scientific American; Aug. 1988; pp. 68–76.
"Photo-Cidnp as a tool for the Study of the Reactivity of Photosensitizing Drugs: The Furocoumarins"; by J. Marko et al.; Photochemistry & Photobiology vol. 47, pp. 1–13, 1988.
"Characterization of a Photoalkylated Psoralen Receptor in HeLa Cells"; by E. Yurkow et al.; *The Journal of Biological Chem.; vol. 262; 1987; pp. 8439–8442*.
"Synthesis of Methyl Derivatives of 8-Desmethylxanthyletine & 8-Desmethylseseline, Potential Antiproliferative Agents"; by P. Rodighiero et al.; J. Heterocyclic Chem., 24, 1987, pp. 485–488.
"Psoralens potentiate ultraviolet light-induced inhibition of epidermal growth factor binding"; by J. Laskin (List continued on next page.)

Primary Examiner—Mary C. Lee
Assistant Examiner—Joseph K. McKane
Attorney, Agent, or Firm—Ratner & Prestia

[57] ABSTRACT

The invention features phototherapeutic compositions comprising Type 1, Type 2, or Type 3 psoralens and methods of using such compounds for treatment of proliferative diseases of skin, blood and bone marrow.

32 Claims, 1 Drawing Sheet

OTHER PUBLICATIONS et al.; proc. Natl. Acad. Sci. USA, vol. 83, 1986, pp. 8211–8215.

"Nitrations of 4',5'-Dihydropsoralenss: A Route to Radiopharmaceutical Precursors"; by Ned Heindel et al.; J. Heterocyclic Chem. 23, 1579 (1986); pp. 1579–1582.

"A possible mechanism of psoralen phototoxicity not involving direct interaction w DNA"; by J. Laskin et al.; Proc. Natl. Acad. Sci. USA, vol. 82, 1985, pp. 6158–6164.

"Aminomethyl Psoralens. Electrophilic Substitution of Hydroxymethylphthalimide on Linear Furocoumarins"; by N. Heindel et al.; J. Heterocyclic Chem., 1985, pp. 73–76.

"Psoralen & Ultraviolet A Effects on Epidermal Ornithine Decarboxylase Induction & DNA Synthesis in the Hairless Mouse[1,2]"; by N. Lowe et al.; Natl. Cancer Institute Mamographs 66:73–76, 1984.

"Cutaneous Squamous–cell Carminoma in Patients Treated w Puva"; by R. Stern et al.; The New England Journal of Medicine; 1984, pp. 1156–1161.

"Transfer Hydrogenations of Furocoumarin Derivatives[1]", by Ned Heindel et al.; American Chemical Society 1983; pp. 3817–3819.

"Epidermal ornithine decarboxylase activity & thymidine incorporation following treatment w ultraviolet A combined w topical 8-methoxypsoralen or anthracene in the hairless mouse"; by R. Gange; British Jouranl of Dermatology (1981) 105, pp. 247–255.

"Ultraviolet Light & Epidermal Polyamines"; by N. Lowe; Journal of Investigative Dermatology, 77:147–153, 1981.

"A Convenient Synthesis of Psoralen Derivatives: Psoralen, 4-Methyl-psoralen & 4-Phenyl-psoralen"; by V. Ahluwalia et al.; Monatshefte für Chemie 111, pp. 877–882, 1980.

"Psoralen Photochemotherapy of Cutaneous Disorders"; by T. Anderson et al.; Ann. Rev. Pharmacol. Toxicol 1980, 20:235–257.

"Ultraviolet Light Induces Epidermal Ornithine Decarboxylase Activity", by N. Lowe; The Journal of Investigative Dermatology, 71:417–418, 1978.

"Synthesis & Characterization of New Psoralen Derivatives with Superior Photoreactivity with DNA and RNA "; by S. Isaacs, Biochemistry, vol. 16, 1977; pp. 1058–1064.

"Induction of the Polyamine–biosynthetic Enzymes in Mouse Epidermis by Tumor–promoting Agents"; by T. O'Brien et al.; Cancer Res. vol. 35, 1975, pp. 1662–1670.

"Repair of DNA Containing Interstrand Crosslinks in *Escherichia coli:* Sequential Excision & Recombination"; by R. Cole; Proc. Nat. Acad. Sci. USA; 1973, pp. 1064–1068.

"Epidermis: disorders of cell kinetics & differentiation"; by E. Farber et al.; Dermatology in General Medicine; pp. 233–247, 1978.

"Psoralens: A Search for More Effective Derivatives for Photochemotherapeutic Regimens[1,2]", by I. Willi et al., National Cancer Institute Monograph, 66:143–147, 1982.

"Transfer Hydrogenations of Furocoumarin Derivatives[1]", by N. Heindel et al.; Biochemistry, 1983, vol. 48, pp. 3817–3818.

CA 90(15):121567g Psoralens. Hearst et al., p. 644, 1979.
CA96(25):213337j Photochemotherapy: . . . derivative, Willis, p. 331, 1982.
CA 102(25):217553s Psoralens: a . . . regimens. Willis et al., p. 299, 1985.
CA114 (17):162520u Sensitizers . . . fats. Sargi et al., p. 623, 1991.

REDUCED AND QUATERNIZED PSORALENS AS PHOTO-ACTIVATED THERAPEUTICS

This application is a continuation-in-part of U.S. patent application Ser. No. 07/633,268, filed Dec. 21, 1990, now U.S. Pat. No. 5,216,176 which is a continuation-in-part of patent application Ser. No. 07/300,869 filed Jan. 23, 1989, now abandoned. This application and the aforementioned parent applications all share common inventorship and assignment.

BACKGROUND OF THE INVENTION

Many proliferative skin diseases (psoriasis, vitiligo, eczema, mycosis fungoides, etc), cancerous conditions (T cell lymphomas), and autoimmune disorders are being treated by the combined utilization of photosensitizing chemicals [applied topically or taken orally] plus ultraviolet light. Terms such as photosensitization, photochemotherapy, photopheresis and PUVA (psoralens ultra violet A radiation) are commonly used to refer to special applications of this method. Clinically useful behavior has been found in such chemical families as heme-derived products, porphyrins, phthalocyanins, and psoralens. The oldest and most established phototherapeutics are the psoralens or linear furocoumarins in which three major commercial pharmaceuticals dominate: 8-methoxypsoralen (methoxsalen or 8-MOP); 4,5',8-trimethylpsoralen (trioxsalen or TMP), and 5-methoxypsoralen (5-MOP).

The widely accepted mechanism of action for psoralens is penetration of the target cell's membrane, intercalation into nuclear DNA, and photo-induced bis 2+2 cycloaddition crosslinking of the double helix. Structural and mechanism studies have shown that the 3,4-double bond and the 4',5'-double bond in psoralen (Formula O below) form cyclobutane adducts with the double bonds in the pyrimidine bases of DNA. This renders the DNA unable to uncoil and serve as a template for new gene expression. Thus, the target cell is rendered non-viable (J. E. Hearst, Chemical Research in Toxicology, 2, 69, 1989; T. F. Anderson and J. J. Vorhees, Ann. Rev. Pharmacol. Toxicol., 10, 177, 1982).

The basic structure of psoralen with the ring numbering structure used herein, is as depicted in Formula O below.

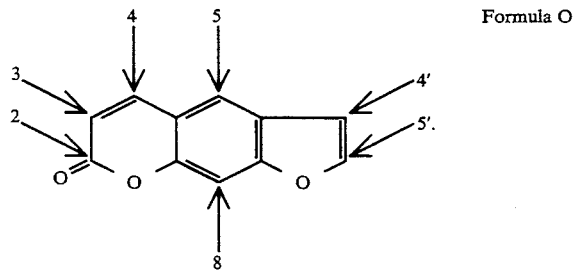

Formula O

A severe limitation to the acceptance of psoralen-based photochemotherapy is the understanding that the natural cellular level repair processes of bi-functional DNA-crosslinks are highly error-prone. Errors in cellular repair processes of true crosslinks translate to mutagenic/carcinogenic events and, in the clinical use of psoralens, represent a significant post-treatment risk of cancer induction. It is known in the art that bent, nonlinear furocoumarins (known as angelicins), which are by their structure limited to the photogeneration of only non-crosslinked mono-adducts, are far less mutagenic/carcinogenic (F. Baccichetti et al., U.S. Pat. No. 4,312,883; R. S. Cole, "Repair of DNA Containing Interstrand Crosslinks in E Coli," Proc. Nat. Acad. Sci. USA, 70, 1064, 1973).

An alternative mechanism is available by which psoralens manifest phototoxicity to a cell. A 22,000 Da protein present in psoralen-sensitive cells has been found to be a specific binding site for photo-activated psoralens. The binding of psoralens to this receptor followed by UVA light activation prevents the binding of epidermal growth factor (EGF), an important cellular messenger for growth and differentiation. Thus, the therapeutic photobiology of psoralens can be explained by a non-DNA target for their molecular activity (N. D. Heindel, J. Van Dongen, B. S. Sachais, J. H. Phillips, M. A. Gallo, and J. D. Laskin, J. Pharm. Sci., 80, 686, 1991).

SUMMARY OF THE INVENTION

The invention features new types of psoralen phototherapeutics and phototherapeutic formulations thereof capable of binding to a non-DNA target in mammalian cells. More specifically, psoralens of the present invention are of three types, which respectively inhibit:

(1) the formation of DNA crosslinks by possessing only a single, pyran-ring unsaturation [Type 1],
(2) the actual crossing of the target cell membrane, necessary to reach the nucleus, by bearing a positive charge [Type 2], and
(3) both of these events by combining the molecular features of Types 1 and 2 into partially reduced quaternary analogs [Type 3].

These compounds, which offer the promise of beneficial photobiology without the risk of forming potentially carcinogenic bis 2+2 cyclobutane crosslinks with DNA, are characterized on the basis of their molecular structure as follows:

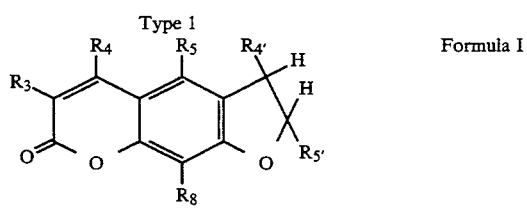

Type 1 — Formula I

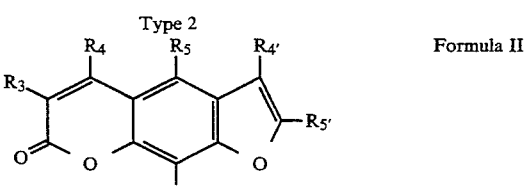

Type 2 — Formula II

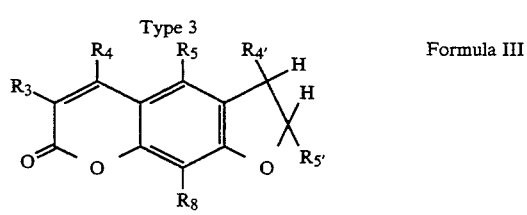

Type 3 — Formula III

The term "psoralen", as used herein refers to any compound having the structure depicted in Formula O above, or any derivative of that structure wherein the 4',5'-double bond is suceptible to reduction.

The invention also features a method of preparing a quaternary amino psoralen substituted in the furan ring, wherein the method includes a first step of effecting a selective bromine atom substitution upon a furan ring methyl in either 4,4',8-trimethylpsoralen or 4,5',8-trimethylpsoralen by reaction with N-bromosuccinimide and benzoyl peroxide, the method further including a second step of aminating the selectively brominated psoralen from step 1 by reaction with any tertiary amine.

A method of treating a proliferative skin disorder in a human patient is also provided by the invention. This method comprises administering to the patient either parenterally, orally, or topically an effective amount of a phototherapeutic compound of the invention, after which the patient is irradiated with UVA.

Similarly, the invention features a method of treating a disease of the blood or bone marrow in a human patient comprising obtaining cells from the blood or bone marrow of the patient, introducing in vitro into the cells a phototherapeutic compound of the invention, exposing the cells so treated to ultraviolet light, and returing the treated irradiated cells to the blood or bone marrow to the patient.

Other features and advantages of the invention will be apparent from the following Detailed Description and from the claims.

The drawing will first be described.

DETAILED DESCRIPTION OF THE INVENTION

Figure 1:
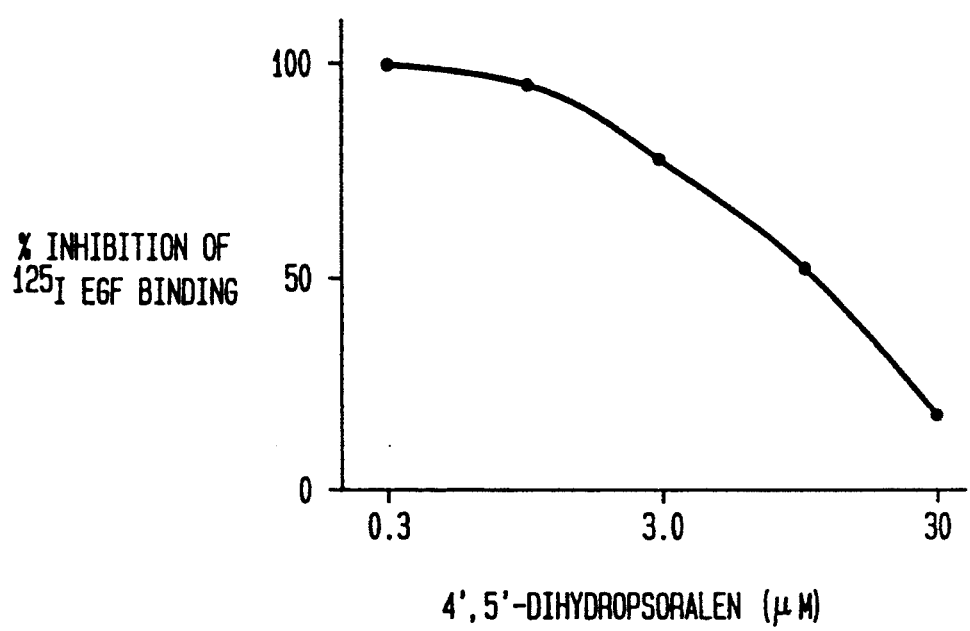
FIG. 1 is a graph depicting the relationship between inhibition of EGF binding to HeLa cells and the concentration of 4',5'-dihydropsoralen

Preparation of Type 1 Psoralens (partially reduced psoralens)

The two double bonds, 3-4 and 4'-5', in a psoralen (see Formula O, above) reduce at significantly different rates with reduction of the furan ring (the 4'-5' double bond) occurring at a faster rate than the 3-4 double bond. Therefore, Type 1 psoralens may be synthesized by catalytic hydrogenation (Method 1) at 1 to 4 atmospheres pressure over 5% palladium supported on carbon. This process can be controlled by use of a micro-pressure regulator to permit termination upon the absorption of one mole equivalent of hydrogen per psoralen. In this method, some reduction (less than 20%) of the 3-4 double bond takes place and chromatographic purification on silica gel permits isolation of pure 4',5'-dihydropsoralens. Because catalytic pressurized hydrogenation is well known in the art no further elaboration herein is considered necessary.

However, a unique catalytic hydrogen transfer reaction without the use of hydrogen gas (Method 2) is unexpectedly facile, generates high yields, and is of great regiospecificity in that it exclusively reduces (under the conditions specified) only the 4'-5' double bond of psoralen leaving the 3-4 bond intact. If catalytic hydrogenation with gaseous hydrogen is used (Method 1), and the contaminating 3-4 hydrogenated byproducts are not completely removed, a less active phototherapeutic results. Saturation at the 3-4 bond leads to biologically inactive products. Double reduction at both double bonds is not a problem with Method 2, termed The Selective Reduction Process. In accordance with this Method 2, a catalyzed transfer of the molar elements of hydrogen from such donors as cyclohexene, 1,3-cyclohexadiene, tetralin, decalin, indane, or limonene in the presence of an alcohol and palladium on carbon is highly selective.

Description of the Selective Reduction Process General case

Any psoralen dissolved in a low molecular weight alcohol (methanol, ethanol, 2-propanol) at the ratio of 1-2 g grams per 100 ml of solvent is combined with 5-30 ml of a hydrogen donor solvent such as 1,3-cyclohexadiene, tetralin, cyclohexene, decalin, or indane. Cyclohexane does not serve well in this application. A metal catalyst such as platinum, palladium, or rhodium supported on carbon at a ratio of 2-10% metal/carbon is added at a ratio of 1-5 g of powdered metal/carbon support for each 2 g of psoralen being reduced. The mixture is stirred at reflux for 0.5 to 6 hours, filtered, evaporated, and the product isolated by chromatography or fractional crystallization. By this process the 4',5'-double bond is reduced without effect upon the 3,4-double bond to produce a 4',5'-dihydropsoralen. While most functional groups [aminos, alkoxys, alkyls, halos, hydroxyls, carboalkoxys (—COOR)], and amides do survive unchanged, nitro groups are rapidly reduced and certain sensitive functions pendant upon the ring undergo hydrogenolysis [e.g., —CH$_2$—R attached to the psoralen system becomes CH$_3$ under these conditions if R is hydroxyl, halogen, or ester (—O—CO—R)].

Suitable phototherapeutic 4',5'-dihydropsoralens [Type 1] are those typified by the generic structure having either hydrogen substitution or single alkyl (or aryl) group substitution at carbons 3, 4, 5, 8, 4', or 5' and no olefinic unsaturation in the furan ring (involving carbons 4' and 5'). Nitro, amino, alkyloxy, aryloxy, aminomethyl, halo functions and other structural variations, but consistent with the presence of a saturated, five membered furan ring, are included where their placement at any carbons on the three ring system does not alter the fundamental structure shown for the 4',5'-dihydropsoralens. Also specifically included in this class are analogs with 5- and/or 8-alkoxy substituents such as methoxy, ethoxy, i-propoxy, and n-propoxy derivatives.

Certain highly polar groups attached at carbon #5 (e.g., nitro, amino, sulfonic acid, and sulfonamide) markedly reduce the biological activity of the class.

Methods for the syntheses of the 4',5'-dihydropsoralens have been published, [see N. D. Heindel, N. Foster, and M. Choudhuri, J. Org. Chem., 48, 3817-3819 (1983); N. D. Heindel, N. Foster, and T. Varkey, J. Heterocyclic Chem., 23, 1579-1582 (1986); and N. D. Heindel, M. Choudhuri, J. Ressner, and N. Foster, J. Heterocyclic Chem. 22, 73-76 (1985)]. These techniques constitute suitable synthetic approaches to these compounds.

Following these general synthetic methods, representative analogs, which include but are not limited to the substances indicated below, may be prepared:

5-N-phthalimidomethyl-4',5'-dihydro-8-hydroxypsoralen
5-N-phthalimidomethyl-4',5'-dihydro-8-methoxypsoralen
5-nitro-4',5'-dihydro-8-methoxypsoralen
5-amino-4',5'-dihydro-8-methoxypsoralen
4,5',8-trimethyl-4'-aminomethyl-4',5'-dihydropsoralen 4,4',8-trimethyl-5'-aminomethyl-4',5'-dihydropsoralen
3,5-dinitro-4',5'-dihydro-8-methoxypsoralen
5-iodo-4',5'-dihydro-8-methoxypsoralen Additional compounds belonging to this class are disclosed below.

Specific Application

Preparation of 4',5'-Dihydropsoralen

A solution was prepared of 1.86 g (0.010 moles) of psoralen (7H-furo[3,2-g][1]benzopyran-7-one) in 200 ml of 95% ethanol, heated to reflux and treated by the addition of 5.0 ml of cyclohexene and a slurry of 5.0 g of 10% palladium on carbon in 30 ml of 95% ethanol. After 30 minutes of reflux with magnetic stirring the medium was filtered, evaporated in vacuo and the residue was recrystallized from 95% ethanol to give 1.36 g (72% yield) of tiny white needles, mp 198°–200° C.

Anal. for $C_{11}H_8O_3$ Calcd: C, 70.23; H, 4.25 Found: C, 70.14; H, 4.00

The presence of electronegative atoms in the pyran-ring of these compounds (Types 1, 2, or 3 psoralens), often contributes to even greater biological activity (lower $IC_{50}$ values). One study has indicated that the mechanism for photo-activated anchoring of psoralens to proteins/amino acids probably involves intermediate formation of an anion radical in the pyranone ring (J. Marko, et al., Photochem. Photobio. 47, 1:1988). Formation of such an anion radical would be facilitated by electronegative attachments. When trifluoromethyl, amino, and nitro groups are attached in the pyran ring, these compounds are excellent therapeutic candidates.

8-Methoxy-4',5'-dihydro-3-nitropsoralen was prepared in 46% yield by nitration of 0.75 g (3.4 mmol) of 8-methoxy-4',5'-dihydropsoralen (synthesis by transfer hydrogenation is described above) with 3 ml of concentrated nitric acid in 7.0 ml of acetic acid at room temperature for 2 hrs. Dilution with water and recrystallization from methanol yielded yellow needles, mp 233°–235° C., Anal Calcd. for $C_{12}H_9NO_6$: C, 54.76; H, 3.45 Found: C, 54.69; H, 3.56

8-Methoxy-4',5'-dihydro-3-aminopsoralen was prepared by the exchange hydrogenation (palladium/carbon plus cyclohexene) described above in 77% yield from the corresponding 3-nitro compound, mp 154°–155° C., by recrystallization from methanol.

Anal Calcd. for $C_{12}H_{11}NO_4$: C, 61.80; H, 4.76 Found: C, 61.82; H, 4.69

Two unique 4-trifluoromethylpsoralens and their dihydro counterparts were prepared through the intermediary of one coumarin building block, 4-trifluoromethyl-7-hydroxy-8-methylcoumarin.

Preparation of 4-trifluoromethyl-7-hydroxy-8-methylcoumarin

A slurry of 2-methylresorcinol (12.4 g, 0.100 mole) and ethyl 4,4,4-trifluoroacetoacetate (18.4 g, 0.100 mole) was added slowly to 100 ml of ice cold sulfuric acid with vigorous stirring. After completion of addition, the solution was allowed to warm to room temperature and was subsequently stirred for 24 hours. The reaction mixture was then slowly added to 500 ml of ice water (300 g ice and 200 ml water) with vigorous stirring. The desired product precipitated from the solution as a light pink solid. The solid was then isolated by vacuum filtration, transferred to a 500 ml beaker, 200 ml of water was added to achieve a slurry and the pH was adjusted to 6 with sodium bicarbonate. The solid was then filtered and recrystallized from ethanol-water to yield 19.5 g (80%) of the desired product. The melting point of the product was 197°–198 ° C.

$^1$H-NMR ($D_3$COD): δ 2.2 (s, 3H, $CH_3$), 5.05 (s, 1H, OH), 6.5 (s, 1H, C3 proton), 6.7 (d, 1H, J=8 Hz, C6 proton), 7.35 (d, 1H, J=8 Hz, C5 proton). IR (KBr): 3414 cm$^{-1}$ (OH), 1713 cm$^{-1}$ (C=O).

Calculated for $C_{11}H_7O_3F_3$: C 54.10 H 2.90 F 23.40 Found: C 54.01 H 2.83 F 23.73

4-Trifluoromethyl-5',8-dimethylpsoralen was prepared in three steps through the initial intermediate, 7-allyloxy-4-trifluoromethyl-8-methylcoumarin. This intermediate was prepared by alkylation of corresponding 7-hydroxycoumarin. To a solution of 4-trifluoromethyl-7-hydroxy-8-methylcoumarin (5.0 g, 0.020 mole) in 100 ml of dry acetone was added 25 g of $K_2CO_3$. Allyl bromide (12.1 g, 100 mmole) was added to the solution and refluxed for 1.5 hours. The reaction was then cooled, filtered and evaporated to dryness. The solid was taken up in 200 ml of chloroform and washed with 3×50 ml of water. The chloroform was removed under reduced pressure and the solid was recrystallized from ethanol to yield the desired compound as white needles, 5.4 g (92%), m.p. 114.5°–115.5° C. $^1$H-NMR (CDCl$_3$): δ 2.35 (s, 3H, $CH_3$), 4.70 (d, 2H, —OCH$_2$, J=4.9 Hz), 5.30–5.56 (c, 2H, =CH$_2$), 5.90–6.37 (m, 1H, —CH=), 6.63 (s, 1H, C3 proton), 6.90 (d, 1H, C6 proton, J=8.79 Hz), 7.55 (d, 1H, C5 proton, J=8.79 Hz). IR (KBr): 1734 cm$^{-1}$.

Calculated for $C_{14}H_{11}O_3F_3$: C 59.15 H 3.87 F 20.07 Found: C 58.92 H 3.72 F 20.11

The next intermediate, the rearranged 6-allyl-4-trifluoro-methyl-7-hydroxy-8-methylcoumarin was prepared from a heterogeneous mixture of 7-allyloxy-4-trifluoromethyl-8-methylcoumarin (2.0 g, 7.0 mmoles) and N,N-diethylaniline (4 ml) at reflux for 6 hours under argon with stirring. The solution was cooled to room temperature and dissolved in 150 ml of chloroform. The chloroform was extracted with 4×50 ml portions of 5% aqueous sodium hydroxide. The basic extract was slowly acidified with concentrated HCl to precipitate the desired product. The solid was filtered and washed with water. The solid was dissolved in chloroform and washed with 3×50 ml of water to remove any inorganic salts. The chloroform was evaporated under reduced pressure to yield 1.3 g (65%) of a light brown solid, m.p. 172°–173° C. IR (KBr): 3406 cm$^{-1}$, 1700 cm$^{-1}$.

Closure of this allyl to the desired 4-trifluoromethyl-5',8-dimethylpsoralen was brought about when 6-allyl-4-trifluoromethyl-7-hydroxy-8-methylcoumarin, 1.00 g (3.50 mmole), was dissolved in 50 ml of anhydrous toluene under an argon atmosphere. To the solution was added 200 mg (3.50 mmoles) of 95% sodium methoxide and 1.35 g (3.50 mmoles) of bis(benzonitrile)palladium (II) chloride and the reaction was refluxed for 3 hours. TLC (CHCl$_3$) of the reaction mixture yielded spots corresponding to the product, benzonitrile, and the starting material. The reaction mixture was filtered through a small silica column using chloroform as the eluent. The resulting solution was evaporated to dryness. The resulting solid was purified by flash chromatography, using chloroform as the eluent, to yield 140 mg of yellow crystals (14%), mp 161°–162.5° C.

$^1$H-NMR (CD$_3$COCD$_3$): δ 2.55 (s, 6H, 2×CH$_3$), 6.67 (s, 1H, C3 proton), 6.80 (s, 1H, C4' proton), 7.70 (s, 1H, C5 proton).

Calculated for C$_{14}$H$_{11}$O$_3$F$_3$: C 59.57 H 3.19 F 20.21
Found: C 59.47 H 3.15 F 20.04

4-Trifluoromethyl-4',8-dimethylpsoralen was prepared stepwise through the first-formed intermediate, 7-acetonyloxy-4-trifluoromethyl-8-methylcoumarin. This was prepared by chloroacetone alkylation of 4-trifluoromethyl-7-hydroxy-8-methylcoumarin. A solution of 10 g of potassium carbonate in 20 ml of dry acetone was added to 1.0 g of 4-trifluoromethyl-7-hydroxy-8-methylcoumarin (4.0 mmoles). To this reaction mixture was then added 1.00 ml of chloroacetone (12.6 moles) and 100 mg of potassium iodide. The reaction was refluxed for 4 hours and then evaporated to dryness under reduced pressure. The crude product was taken up in chloroform and washed with 3×50 ml of water. The solution was evaporated to dryness and recrystallized from toluene to yield white crystals, 5.2 g (88%), mp. 143°–144.5° C. $^1$H-NMR (CDCl$_3$): δ 2.35 (s, 3H, CH$_3$), 2.41 (s, 3H, CH$_3$), 4.71 (s, 2H, OCH$_2$), 6.72 (d, 2H, J=9.1 Hz, C5 and overlapping C3), 7.60 (d, 1H, J=9.1 Hz, C6).

Calculated for C$_{14}$H$_{11}$O$_4$F$_3$. 0.25 H$_2$O: C 55.17 H 3.81
Found: C 54.73 H 3.46

A heterogeneous mixture of 3.00 g of 7-acetonyloxy-4-trifluoromethyl-8-methylcoumarin (10 mmole), 1.35 g of potassium hydroxide, and 165 ml of water was refluxed for 4 hours. The resulting homogeneous mixture was cooled to 0° C. and acidified with 1N HCl accompanied by vigorous stirring to precipitate the product. The product was separated by filtration, dried, and recrystallized from ethanol to yield 1.6 g (57%) of the desired psoralen [4-trifluoromethyl-4',8-dimethylpsoralen, mp 185°–186° C.

Calculated for C$_{14}$H$_9$O$_3$F$_3$: C 59.57 H 3.19 F 20.21
Found: C 59.36 H 3.05 F 19.93

Listed below are candidate 4',5'-dihydro psoralens of Type 1 which were prepared, using methods similar to that described above for 4',5'-dihydropsoralen using the Selective Reduction Process; in each case, the corresponding fully aromatic psoralens, known in the literature or prepared as described herein, was converted to yield the following products:

3-carboethoxy-4',5'-dihydropsoralen, mp 211°–213° C., 52% yield
4,5',8-trimethyl-4',5'-dihydropsoralen, mp 159°–161° C., 62% yield
4,4',8-trimethyl-4',5'-dihydropsoralen, mp 131°–133° C., 64% yield
8-methoxy-4',5'-dihydropsoralen, mp 164°–165° C. 71% yield
8-methoxy-3-iodo-4',5'-dihydropsoralen, mp 204°–205° C., 59% yield
5-methoxy-4',5'-dihydropsoralen, mp 167°–168° C. 57% yield
8-hydroxy-4',5'-dihydropsoralen, mp 198°–199° C., 62% yield
8-[2-(N,N-dimethylamino)ethoxy]-4',5'-dihydropsoralen HCL salt, mp 223°–225° C. 47% yield
4-trifluoromethyl-4',5'-dihydro-4',8-dimethylpsoralen, 58% yield
4-trifluoromethyl-4',5'-dihydro-5',8-dimethylpsoralen, mp 155°–156° C. 61% yield All of these substances can be recognized by their distinctive proton NMR spectra in which the formerly aromatic furan-ring proton resonances (which appear at ca. 7 to 8 ppm in DMSO-d$_6$) vanish and are replaced with upfield aliphatic resonances (which appear at ca. 3 to 5 ppm in DMSO-$_6$). In the case of the 4-trifluoromethylpsoralens, long range F-to-H splitting is seen in the proton-NMR into the proton on carbon #5.

Preparation of Type 2 Psoralens (Quaternary Psoralens)

The positively charged or quaternary amino psoralens (whose charge prohibits membrane penetration) upon photoactivation inhibit the binding of radioiodinated epidermal growth factor at the protein receptor. Unexpectedly, these quaternary agents display the same beneficial photobiology found in other psoralens at concentrations equal or less than that of clinically active agents. To prepare such agents a unique free radical bromination was used which places a displaceable halogen on a furan-ring methyl (at C-5' or C-4'). Other multiply brominated psoralens (with halogens on the ring carbons as well as on the furo-methyl substitutent) can be generated by the use of elemental bromine. These halomethyl halogens can then be displaced with the requisite amine.

The invention should not be construed as being limited to any particular anion for the quaternary amine because in aqueous media, ionic dissociation separates the anion from the cation and it is within the organic cation wherein the biological activity resides.

Halogen-pendant psoralens, generated as intermediates in the course of these syntheses, are also highly active phototherapeutics in their own right. Psoralens with pendant trifluoromethyl groups and bromo moieties have IC$_{50}$'s of the same (or better) magnitude as those of the clinically important agents such as 8-MOP and TMP. The syntheses of the 4-trifluoromethylpsoralens has been described in the preparation of Type 1 compounds. The examples below illustrate the preparation of the halopsoralen and then its amination.

Bromination Reaction

Preparation of 5'-Bromomethyl-4,8-dimethylpsoralen

Into a 10 ml round bottom flask fitted with a Claisen head containing a septum and a reflux condenser was placed 0.10 g (0.44 mmoles) of 4,5',8-trimethylpsoralen (trioxsalen or TMP), 0.089 g (0.50 mmoles) of N-bromosuccinimide, and 5.0 ml of anhydrous chloroform. The reaction vessel was blanketed continuously with nitrogen and the reaction mixture was brought to reflux while a solution of 0.060 g (0.25 mmoles) of benzoyl peroxide in 1.0 ml of anhydrous chloroform was added in portions of 0.2 ml every 15 minutes over 1.25 hours. Reflux was continued for another 1.5 hours and the resulting mixture was cooled to room temperature, then washed with saturated aqueous sodium bicarbonate (3×2 ml), and water (2×2 ml). The organic layer was dried over magnesium sulfate, filtered, and the solvent was evaporated under reduced pressure. The product was recrystallized from methanol to yield 0.11 g (87%) of pale yellow crystals, mp 218°–220° C. (decomp.); IR (KBr pellet) 1705 (C=O) and 1632 cm$^{-1}$ (C=C); $^1$H- NMR (CDCl$_3$) δ 2.49 ppm (d, 3H, 4—CH$_3$, J=1.15 Hz), 2.61 ppm (s, 3H, 8—CH$_3$), 4.61 ppm (d, 2H, 5'—CH$_2$), 6.27 ppm (q, 1H, 3—H, J=1.15 Hz), 6.81 ppm (1H, 4'—H), 7.61 ppm (s, 1H, 5—H).

Anal. Calc for $C_{14}H_{11}BrO_3$: C, 54.90; H, 3.59. Found: C, 55.06; H, 3.69.

In this, and in subsequent brominations with N-bromosuccinimide and benzoyl peroxide, it is of note that the insertion of a bromine atom occurs first upon the methyl in the furan ring before any other methyl elsewhere in the molecule is attacked. This observation makes possible the clean synthesis of —$CH_2$—Br upon the furan ring which leads, in the subsequent syntheses, to the highly active quaternaries prepared by aminolysis of these benzylic-like bromides.

4'-Bromo-5'-bromomethyl-4,8-dimethylpsoralen

A solution of 4,5',8-trimethylpsoralen (TMP), 1.00 g (4.40 mmoles), in 20 ml of chloroform containing 1.78 g (10.0 moles) of N-bromosuccinimide was brought to reflux under nitrogen and a solution of benzoyl peroxide (0.5 g dissolved in 4 ml of chloroform) was added dropwise. Refluxing was continued for 6 hours and the resulting pale yellow solution was cooled to room temperature, washed with a saturated aqueous solution of sodium bicarbonate (3×5 ml) and then with $H_2O$ (2×5 ml). The organic layer was dried over anhydrous magnesium sulfate and the solvent removed in vacuo to yield 1.82 g of the crude product.

The remaining components in the supernatant were separated by HPLC using a silica column (Porasil 10I 8 mm Radial Pak) with a 1:1 mixture of chloroform and hexane as the eluent. The product was obtained in a total yield of 0.87 g (2.30 mmoles) 51%, mp 235°–237° C., $^1$H-NMR(500 MHz) in $CDCl_3$, δ 2.53 ppm (d, 3H, C4—$CH_3$, J=1.13 Hz), 2.61 ppm (s, 3H, C8—$CH_3$), 4.66 ppm (2H,C5'—$CH_2$), 6.31 ppm (q, 1H, C3—H, J=1.10 Hz), 7.53 ppm (s, 1H, C5—H). IR(KBr): 1714 $cm^{-1}$, 2364 $cm^{-1}$.

Anal. calcd for $C_{14}H_{10}Br_2O_3$: C, 43.52; H, 2.69; Br, 41.45. Found: C, 42.98; H, 2.90; Br, 41.94.

5'-Bromo-4'-bromomethyl-4,8-dimethylpsoralen

This compound was prepared by the addition of molecular bromine 0.09 g (0.59 mmoles) in 5 ml of chloroform to a solution of 4,4',8-trimethylpsoralen, 0.07 g or 0.29 moles, dissolved in 10 ml of chloroform. The mixture was stirred at room temperature in the dark for 48 hr and then evaporated to dryness to yield 0.12 g of crude product. This crude sample resulted in 3 spots on a TLC plate using methylene chloride as the elutant. Separation using Preparatory Thick Layer Chromatography resulted in obtaining the title compound in a yield of 0.080 g (70%): $^1$H-NMR in $CDCl_3$ δ 2.53 ppm (d, 3H, C4—$CH_3$, J=0.88 Hz), 2.58 ppm (s, 3H,$CH_3$), 4.57 ppm (2H, C4'—$CH_2$), 6.30 ppm (q, 1H, C3—H, J=0.89 Hz), 7.64 ppm (s, 1H, C5—H). The substance was quaternized directly without further purification.

3,5'-Dibromo-4'-bromomethyl-4,8-dimethylpsoralen 4,4',8-Trimethylpsoralen, 0.19 g (0.82 mmoles) was dissolved in 15 ml of chloroform and stirred for 15 minutes after which 0.13 g (4.06 mmoles) of bromine was added. After 43 hours of continuous stirring at room temperature, thin layer chromatography analysis in methylene chloride yielded a new spot with an Rf=0.75. The solvent was removed in vacuo to yield 0.37 g of crude product which was recrystallized from chloroform to give 0.33 g (0.71 mmoles) of the title compound in 87% yield, mp 267°–268° C. $^1$H-NMR (500 MHz in $CDCl_3$), δ 2.60 ppm (s, 3H, $CH_3$), 2.75 ppm (s, 3H, $CH_3$), 4.58 ppm (s, 2H, $CH_2$), 7.71 ppm (s, 1H, C5—H).

Anal. calcd for $C_{14}H_9Br_3O_3$: C, 36.13; H, 1.94; Br, 51.61. Found: C, 35.99; H, 1.87; Br, 51.90.

Amination Reactions

From these brominated precursors, quaternary amines can readily be prepared as described below.

5'-[(N-Pyridinium)methyl]-4,8-dimethylpsoralen Bromide Salt

Pyridine 0.10 g (1.24 mmoles) was added dropwise to a solution of the previously described 5'-bromomethyl-4,8-dimethylpsoralen, 0.21 g (0.67 mmoles), in 15 ml of toluene while the mixture was stirred continuously. The reaction mixture was brought to reflux under nitrogen for a total time of 14 hours after which precipitation was observed. The resulting solution yielded two spots by TLC analysis in an eluent mixture of hexane, chloroform, and methanol in a 3:1:1 ratio, $R_f$=0.75 and $R_f$=0. Addition of 10 ml of ether to this solution resulted in massive precipitation. The precipitate was filtered and washed with ether to obtain the title compound in a yield of 0.14 g (53%). TLC analysis of this compound in the same eluent system yielded one spot on the baseline, mp 251°–251.5° C. $^1$H-NMR in $CDCl_3$ δ 2.49 ppm (d, 3H, C4—$CH_3$ J=1.15 Hz), 2.62 ppm (s, 3H, C8—$CH_3$), 5.48 ppm (2H, C5'—$CH_2$), 6.27 ppm (q, 1H, C3—H J=1.15 Hz), 6.90 ppm(1H,C4'—H), 7.64 ppm (s, 1H, C5—H), [7.47 ppm (m, 2H), 7.58 ppm (m, 1H), 8.10 ppm (d, 2H) all pyr-H].

Anal. calcd for $C_{19}H_{16}NBrO_3.25$ $H_2O$: C,58.39; H, 4.26; N, 3.58, Br, 20.47. Found: C, 58.14; H, 4.13; N, 3.36; Br, 20.68.

4'-Bromo-5'-N-[(4-ethylpyridinium)methyl]-4,8-dimethylpsoralen bromide salt

4'-bromo-5'-bromomethyl-4,8-dimethylpsoralen, 0.19 g (0.62 mmoles), was dissolved in 15 ml of benzene and pyridine 0.33 g (3.10 mmoles) in 5 ml of chloroform was added dropwise over a period of 15 minutes. The resulting mixture was refluxed and stirred for a total of 3 hours after which precipitation was observed. The precipitate was filtered, washed with 2×5 ml portions of benzene and then with 2×5 ml portions of ether to yield 0.19 g of crude material. TLC analysis in an eluent mixture of hexane, chloroform and methanol in ratio of 3:1:2 yielded a spot with an $R_f$=0.2. The crude product was recrystallized from methanol to obtain analytically pure material 0.15 g (58%) mp 240°–241° C. $^1$H-NMR in $CDCl_3$ δ 2.47 ppm (s, 3H, C8—$CH_3$), 2.53 ppm (d, 3H, C4—$CH_3$, J=1.16 Hz), 3.30 ppm (2H, C5'—$CH_2$), 6.30 ppm (q, 1H, C3—H J=1.16 Hz), 7.73 ppm (s, 1H, C5—H), [1.37 ppm (t, 3H, J=7.6 Hz), 3.03 ppm (q, 2H J=7.6 Hz), 8.08 ppm (d, 2H J=6.7 Hz ), 9.01 ppm ( d, 2H, J=6.7 Hz ), pyr-H ].

Anal. Calcd for $C_{21}H_{19}NBr_2O_3$: C, 50.19; H, 3.98; N, 2.79. Found: C, 50.51; H, 3.89; N, 2.78.

5'-Bromo-4'-N-[(4-ethylpyridinium)methyl]-4,8-dimethylpsoralen bromide salt

To a solution of 5'-bromo-4'-bromomethyl-4,8-dimethylpsoralen 0.080 g (0.21 mmoles) in 10 ml of toluene was added 0.5 ml of 4-ethylpyridine. The mixture was stirred for 30 minutes at room temperature and then refluxed for 3 hours. The resulting precipitate was filtered, washed with toluene and then with ether to yield 0.06 g (0.11 mmoles) 50% of the title compound, mp 285°–286° C. $^1$H-NMR δ 2.50 ppm (3H, $CH_3$), 2.51 ppm (3H, $CH_3$), 6.04 ppm (2H, $CH_2$), 6.44 ppm (1H, C4—H), 8.02 ppm (1H, C5—H), [1.25 ppm (t, 3H, $CH_3$ J=7.50 Hz), 2.90 ppm (q, 2H, $CH_2$ J=7.50 Hz), 8.05 ppm (d, 2H, J=6.7 Hz), 9.01 ppm (d, 2H, J=6.70 Hz), pyr-H].

Anal. Calcd for $C_{21}H_{19}NBr_2O_3$: C, 51.12; H, 3.85; N, 2.84; Br, 32.45. Found: C, 50.88; H, 3.50; N, 2.99; Br, 32.01

3,5'-Dibromo-4'-N-[(4-ethylpyridinium)methyl]-4,8-dimethylpsoralen bromide salt Preparation of this substance was carried out using a method similar to that described immediately above for the 4-ethylpyridinium bromide salt. A solution of 3,5'-dibromo-4'-bromomethyl-4,8-dimethylpsoralen 0.15 g (0.32 mmoles) and 0.10 g (0.93 mmoles) of 4-ethylpyridine was prepared in 15 ml of toluene. The mixture was stirred at 30° C. for 5 h. The resulting precipitate was filtered and washed with ether to obtain a crude material in a yield of 0.2 g. The crude product was recrystallized from methanol to yield 0.10 g (0.18 mmoles) 55% yield of the title compound, mp 254°–255° C. $^1$H-NMR in DMSO δ 2.49 ppm (s, 3H, $CH_3$), 2.66 ppm (s, 3H, $CH_3$), 6.04 ppm (s, 2H, C4'—$CH_2$), 8.15 ppm (s, 1H, C5—H), [1.25 ppm (t, 3H, J=7.5 Hz), 2.93 ppm (q, 2H, J=7.5 Hz), 8.06 ppm (m, 2H, J=6.5 Hz), 9.01 ppm (m, 2H, J=6.5 Hz), pyr-H]. IR(KBr): 1726 $cm^{-1}$, 2363 $cm^{-1}$.

Anal. calcd for $C_{21}H_{18}NBr_3O_3$: C, 44.06; H, 3.15; N, 2.45; Br, 41.96. Found: C, 43.76; H, 3.01; N, 2.46; Br, 41.76.

A diversity of compounds of Type 2 can be generated by facile displacement with a tertiary amine in the manner described above, from the requisite halomethyl precursor psoralens. Examples of suitable amines, include trimethylamine, triethylamine, pyridine and other alkyl pyridines, N, N-dimethylaniline, and N,N-dimethylcyclohexylamine although the invention should not be construed as being limited to these amines, as many other amines can also be used. Yields on the alkylation typically range from 40–75%. While the bromide salts are the ones directly isolated from the medium, any anionic salt [prepared by ion exchange on a column loaded in the desired anion form], displays similar photobiology.

One may also alkylate the halomethyl psoralen with secondary and primary amines and in a subsequent step then quaternize these. This technique has special value in the preparation of Type 3 psoralens described herein below. Other specific analogs prepared by these methods include:

5'-[(N,N,N-trimethylammonium)methyl]-4,4',8-trimethylpsoralen iodide salt, mp 190°–191° C., 66% yield 5'-[N-(4-ethylpyridinium)methyl]-4,8-dimethylpsoralen bromide salt, mp 226°–228° C. 57% yield 5'-[(N,N-dimethylammonium)methyl]-4,8-dimethylpsoralen chloride salt, 71% yield (mp 132°–134° C. for the free base)

5'-[(N,N,N-trimethylammonium)methyl]-4,8-dimethylpsoralen bromide salt, mp 230°–235° C. 48% yield

Preparation of Type 3 Psoralens
(partially-reduced quaternary)

Quaternary ammonium salts do not cross a cell membrane unless a specific active transport mechanism exists. As a structured ancillary benefit in precluding the crosslinking of nuclear DNA, and thereby minimizing mutagenic/carcinogenic side effects, Type 3 psoralens have been developed which combine the absence of furanside unsaturation with quaternary salt structure.

In a manner to that described for Type 2 psoralens above, the invention should not be construed as being limited to any particular anion for the quaternary amine because in aqueous media, ionic dissociation separates the anion form the cation and it is within the organic cation wherein the biological activity resides.

Direct reduction of the quaternary compounds (Type 2) described above by catalytic hydrogenation (pressurized hydrogen, palladium or platinum catalyst) was not a successful route for the synthesis of this class of psoralens because the process reductively removed ("hydrogenolysis") the ammonium group and then reduced the 4',5'-double bond. The selective hydrogen transfer process did provide low yields (10–20%) of 4',5'-dihydro quaternary products by switching to platinum or rhodium catalysts, using acid-free solvents, and adding a trace (ca 1%) of sodium nitrite. These techniques which minimize hydrogenolysis are well known in the art (R. L. Augustine, "Catalytic Hydrogenation," Marcel Dekker Publishing, N.Y., 1965, p. 137).

As an alternative method, the halomethyl psoralens described above can be first aminated with a secondary amine to generate a tertiary amino psoralen, which can then be reduced by the selective hydrogen transfer process and subsequently methylated. Hydrogenolysis is not a significant problem in the reduction of an unsaturated tertiary amine. Thus, by condensation of 4,8-dimethyl-5'-bromomethylpsoralen with dimethylamine, a 71% yield (mp 132°–134° C.) of 5'-[(N,N-dimethylamino)methyl]-4,8-dimethylpsoralen was obtained. This was reduced using the method described above and the crude 4',5'-dihydro was methylated in situ with methyl iodide to 5'-[(N,N,N-trimethylammonium)methyl]-4',5'-dihydro-4,8-dimethylpsoralen iodide salt (mp 230°–235° C.) in 58% yield.

Similar, examples of Type 3 agents prepared as described include:

5'-[(N-morpholino-N-methylammonium)methyl-4',5'-dihydro-4,8-dimethylpsoralen iodide salt 4'-bromo-5'-[(N,N,N-trimethylammonium)methyl]-4',5'-dihydro-4,8-dimethylpsoralen iodide salt

Pharmacological Assay Techniques

A sensitive in vitro assay can be used to assess the efficacy of the phototherapeutic pharmaceuticals of the invention. Using this assay, large numbers of furocoumarins can be screened and characterized on the basis of photo-induced activity in psoralen-responsive cell lines.

Historically, the uncovering of clinically promising phototherapeutics has arisen from the serendipitous discoveries of folk medicine utilization of natural products. However, for laboratory products, extensive animal trials (for which few good bioassay models exist for disease of human skin) were required before human trials could begin.

The correlations between such animal studies and human photobiology have not been uniformly promising. We have discovered that certain biochemical assays at the cellular level have preclinical predictive merit for beneficial photopharmacology. These assays are based on sound pharmacological principles of agonist-receptor interaction. For a discussion on these in vitro assays see J. D. Laskin, E. Lee, E. Yurkow, D. Laskin, M. Gallo, Proc. Natl. Acad. Sci. (USA) 82:6158 (1985).

Prior to the discovery of the methodologies described herein, structure-activity studies on the drugs disclosed and herein would have required both extensive animal and human testing. The reason was simply that no suitable in vitro models existed for the pharmacological prescreening of large numbers of candidate phototherapeutics. Obviously, the use of live animal models is a serious limitation with regard to laboratory working time, expense, and humane considerations. Rapid in vitro assays utilizing cells in culture are, if available, greatly advantageous in the testing of large numbers of potential phototherapeutics. These methods, if successful, can be used as prescreens for active compounds and thereby reduce the number of substances which must eventually undergo the more systemic, in vivo, chronic toxicity/efficacy testing.

The primary in vitro screen for the phototherapeutics described herein is based on our discovery that beneficial phototherapeutics inhibit binding in cells of epithelial origin with epidermal growth factor (EGF). Furthermore, the degree of effective competition in this EGF binding assay relates to the phototherapeutic effect of the test agent. [J. Laskin, E. Lee, D. Laskin, M. Gallo, Proc. Nat. Acad. Sci. (U.S.A.) 83: 8211 (1986)].

Epidermal growth factor is a low molecular weight polypeptide which binds to cell surface receptors and which is known to be an important regulator of growth in those cells which possess these particular cell surface receptors. Psoriasis, mycosis fungoides, eczema, cancer, and similar proliferative diseases are often characterized by abnormal cell growth regulation which may be related to the action of EGF on the cells in question. Application of PUVA therapy to correct skin disorders, especially psoriasis, is one clinical expression of photochemotherapy. The use of the assay described herein is based on the observation that phototherapeutics are extremely potent inhibitors of binding of epidermal growth factor to cell surface receptors in mammalian cells including humans and that inhibition of this binding arrests the proliferative disorder. This binding assay was performed in the cell culture laboratory.

Inhibition of EGF binding is dependent on dose of the phototherapeutic and on the quanta of light in the 320–400 nm wavelength (ultraviolet light A). It is also structure-dependent, that is, there is a direct correlation between those specific phototherapeutics currently used that are clinically active and their ability to inhibit the binding of epidermal growth factor to its receptor.

Representative examples of the compounds described and claimed herein were tested in this assay for biological activity and found to be potent inhibitors of epidermal growth factor binding. Inhibition of EGF binding was rapid, dependent on concentration, and required light activation. These findings directly demonstrate that the newly synthesized compounds are potential phototherapeutics for human proliferative diseases. A description of this assay follows.

The ability of the above compounds in the presence of ultraviolet light, to inhibit epidermal growth factor binding to its cell surface receptor is directly related to its phototherapeutic potential. To assay these compounds for this biological activity, human cells (HeLa) grown in vitro were used. Cells ($1.8 \times 10^4/cm^2$) were inoculated into 5 cm culture dishes in growth medium consisting of Dulbecco's modified Eagle's medium supplemented with 10% newborn calf serum. After 4–5 days at 37° C. in a humidified $CO_2$ incubator, the cells were washed three times with 2 ml of phosphate buffered saline and then incubated with the different phototherapeutics in 2 ml of Earle's salt solution supplemented with 5.2 mM D-glucose/25 mM Hepes buffer, pH 7.2. Control cultures were incubated in 2 ml of Earle's salt solution in the absence of the test drugs. After 30 minutes, the cells were then exposed to ultraviolet light (UVA, 320–400 nm) emitted from a bank of four BLB fluorescent light tubes (F40BL/Sylvania) placed approximately 10 cm above the cell culture plates. The incident light delivered onto the culture plates was 3.4 mW per $cm^2$ as measured with an International Light UV-Radiometer and the cells received 2.1 $J/cm^2$ of UVA light. After this light exposure, the cells were rinsed with phosphate buffered saline and submitted for assay of epidermal growth factor binding. Phototherapeutic treated cells were then incubated for 2 hours at 4° C. with 2 ml of binding buffer (Dulbecco's modified Eagle's medium/25 mM Hepes buffer, pH 7.2) containing 2 nM labeled epidermal growth factor ($^{125}$I-EGF, specific activity 200 Ci/g).

Nonspecific binding was determined by incubating separate plates of cells with buffer containing the radioligand and excess unlabeled epidermal growth factor (1 microgram/ml). The binding reaction of the radioligand to the cells was terminated by aspirating the binding buffer from the culture dishes and washing the cells four times with ice cold phosphate buffered saline. The cells were then solubilized with 2 ml of 0.2M NaOH and duplicate 0.5 ml aliquots were taken for gamma counting. Specific binding of epidermal growth factor to its receptor was calculated by subtracting nonspecifically bound material from the total. Under the conditions of the assay, specific epidermal growth factor receptor binding represented greater than 80% of the total bound to the cells. The assay may be performed on a variety of cells which possess EGF receptors.

As a specific example of this assay, HeLa cells were treated with 4',5'-dihydropsoralen, followed by ultraviolet light exposure and then by measurement for epidermal growth factor binding. The data can be presented as a curve of epidermal growth factor receptor binding to the cells as a percentage of untreated cells. FIG. 1 is an example of 125-I EGF binding inhibition of 4',5'-dihydropsoralen and UVA. The concentration inhibiting epidermal growth factor binding to the cells by 50% (the $IC_{50}$ value) is determined from the curve.

This value is shown in Table I for a variety of phototherapeutics. Note that all compounds claimed herein are potent inhibitors in the micromolar concentration range for $IC_{50}$'s. While most of the psoralens claimed herein possess methyls at carbons #4 and #8, we did in fact prepare and evaluate several of the 4-methyl and the 8-methyl psoralen counterparts. In virtually every case higher biological activities were observed in the 4,8-dimethylpsoralens of Type 1, Type 2, and Type 3.

An example of such biological activity is depicted in FIG. 1.

TABLE 1

Comparison of the Biological Activity of Novel Phototherapeutics Using Epidermal Growth Factor Binding Inhibition Assay

| Compounds** | $IC_{50}$ (IM)* |
|---|---|
| 4,5',8-trimethylpsoralen (trioxsalen or TMP) | 6.6 |
| 5-methoxypsoralen (5-MOP) | 1.6 |

TABLE 1-continued

Comparison of the Biological Activity of Novel Phototherapeutics Using Epidermal Growth Factor Binding Inhibition Assay

| Compounds** | $IC_{50}$ (iM)* |
|---|---|
| 4,5',8-trimethyl-4',5'-dihydropsoralen | 7.0 |
| 3-nitro-4,5',8-trimethyl-4',5'-dihydropsoralen | 24.0 |
| 4',5'-dihydropsoralen | 11.0 |
| 3-carboethoxy-4',5'-dihydropsoralen | 4.9 |
| 5-methoxy-4',5'-dihydropsoralen | 2.8 |
| 5'-bromomethyl-4,8-dimethylpsoralen | 1.5 |
| 5'-bromomethyl-4'-bromo-4,8-dimethylpsoralen | 3.6 |
| 5'-[(N-pyridinium)methyl]-4,8-dimethylpsoralen bromide salt | 0.74 |
| 4'-[(N,N,N,-trimethylammonium)methyl]-4,5',8-trimethylpsoralen iodide salt | 5.0 |
| coumarin | >100*** |

*$IC_{50}$, concentration of each compound inhibiting 125-I-EGF binding to HeLa cells by 50%
**Following treatment of the cells with the phototherapeutic they were pulsed with 2.1 J/cm$^2$ of ultraviolet light
***Highest concentration tested These substances mentioned above and others which correspond to the general structures of Types 1, 2, and 3 psoralens, have beneficial photocosmetic and photochemotherapeutic effects. The effects can be outlined as follows. In combination with light (UVA), they are able to induce a regional melanogenesis (tanning), to inhibit the binding of epidermal growth factor (EGF), and to act as antiproliferative agents for a wide variety of cells which possess EGF receptors. It is these photoactivated properties—and their derivative clinical effects—which constitute the utility of these compounds.

Formulation and Administration

The compounds are usually diluted prior to use and may be administered orally, intravenously, parenterally or topically, i.e., in the form of a lotion or ointment. The pharmaceutical compositions according to the present invention are suitable for use in effecting photochemical sensitivity on the skin of a mammal, particularly a human patient or subject, and comprise an effective amount of a compound of the invention in association with a pharmaceutically acceptable carrier or diluent. Such compositions are well known in the art, and reference is made to U.S. Pat. Nos. 4,124,598 and 4,130,568 for representative examples, the disclosures of which are incorporated by reference herein. The procedure for preparation of such compositions is totally conventional in the art. For oral treatment, the active ingredient is generally formulated in tablets or in gelatin capsules. In such case, the diluent may, if desired, be eliminated, although it is generally present. For topical applications, solutions or ointments may be prepared and employed. These may be formulated with any one of a number of pharmaceutically acceptable carriers, as is well known in the art. Administration may be, for example, in the form of tablets, capsules, powders, syrups, or solutions, or as already stated in the form of ointments, creams, or solutions for topical use. For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient. In general, an oral dosage regimen will include about 5 mg to about 50 mg per kg of body weight, with a dose in the neighborhood of about 5-10 mg per kg generally being preferred. Such administration and selection of dosage and unit dosage will of course have to be determined according to established medical principles and under the supervision of the physician in charge of the therapy involved. For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carrier of types already mentioned. A typical formulation for a phototherapeutic lotion (1% lotion) is:

| | |
|---|---|
| propylene glycol | 25 ml |
| triethanolamine | 1 ml |
| water | 12 ml |
| oleic acid | 1.5 grams |
| polyethylene glycol 400 monostearate | 10.5 grams. |
| silicon fluid DC-200 | 10 ml |
| carbopol 934, 2% mucilage | 50 grams |
| psoralen or new therapeutic | 1 gram |

Following administration of the compound, the patient is irradiated with UVA at a dose ranging from 0.2 to 15 joules/cm$^2$. The amount and duration of irradiation will depend upon a number of factors including the type and the extent of the disease being treated, the age of the patient etc. and will be apparent to one skilled in the art. The frequency of treatment will also depend upon factors such as those listed above and will also be apparent to one skilled in the art.

Method of Treating Blood or Bone Marrow

The compounds of the invention may also be used to treat diseases of the blood or bone marrow in a patient by first, obtaining cells from the blood or bone marrow of the patient; second, treating the cells in vitro with a Type 1, 2, or 3, psoralen compound; third, exposing the cells so treated to ultraviolet light; and, fourth, returning the cells to the patient' blood stream or bone marrow. Or, alternatively, the patient may be treated by administering the compound to the patient as described above, removing cells of the blood or bone marrow from the patient, irradiating such cells and then returning the cells to the patient's blood or bone marrow.

Blood cells may be obtained from a patient using any ordinary conventional technique. Bone marrow may be obtained using established protocols available to those in the art and described from example in Kitano et al. (1991, Blood 77:1699–1705), or Folks et al. (1988, Science 242:919–922). White blood cells may be separated from pigmented cells (red blood cells) and other factors using the common technique of leukopheresis. If necessary, subpopulations of cells of interest from either the blood or bone marrow may be separated from the remainder of cells in the sample using a combination of techniques including centrifugation and flow cytometry. Cells so isolated are then either irradiated (in the case of the patient to whom the drug has already been administered), or they are treated with the compound of choice in a manner similar to that described above for the treatment of HeLa cells in culture followed by irradiation. Essentially, the phototherapeutic compound is dissolved in an isotonic buffered solution and is added to the cells in a therapeutically effective amount to be determined by the extent and type of disease being treated, and the number of cells in the sample. After a period of incubation, treated cells are exposed to ultraviolet light (UVA, 320–400 nm) as described above.

After exposure to light, the cells are washed in an isotonic, buffered solution and are returned to either the patient's blood or bone marrow using conventional technology.

Examples of diseases treatable by this method include Acquired Immunodeficiency Syndrome, Cutaneous T Cell Lymphoma, Scleroderma, Vitiligo, Rheumatoid Arthritis and other arthridides, Myasthenia Gravis, Multiple Sclerosis, Lupus Erythematosus, and the like.

The compounds of the invention which are capable of intercalating into double-stranded nucleic acid, i.e., 4',5'-dihydropsoralens, may also be used to eliminate or reduce the levels of infectious agents in blood. Blood may be treated with such a compound under the conditions described above and be subsequently irradiated with UVA. This treatment has advantages over known treatments which use psoralen compounds that also form crosslinks in double stranded nucleic acid. In the latter case, residual psoralen remaining in the blood sample is potentially quite mutagenic to a patient receiving such blood, e.g., during a transfusion; whereas, in the former case, residual 4'5'-dihydropsoralen is potentially far less mutatgenic to a recipient of the blood because of the inability of these compounds to form crosslinks in the DNA.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A photochemotherapeutic compound wherein said compound is a psoralen from the group consisting of
   (A) a compound having the structure of Formula I

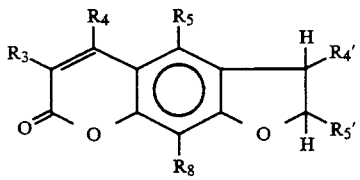

wherein $R_3$ is H, amino, nitro, carboethoxy, halo or alkyl,
wherein $R_4$ is H, methyl or trifluromethyl,
wherein $R_5$ is H or alkoxy,
wherein $R_4'$ and $R_5'$ are alkylamino or halo, and
wherein $R_8$ is H, alkyl, halo, haloakyl or alkoxy,
(B) a compound having the structure of Formula II

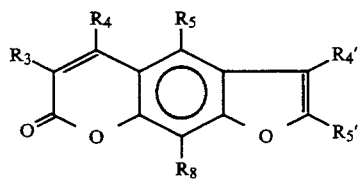

wherein $R_3$ is H, alkyl or halo,
wherein $R_4$ is H, methyl or trifluoromethyl,
wherein $R_5$ is H or alkoxy,
wherein $R_4'$ and $R_5'$ are alkylammonium, alkyl or halo, and at least one of $R_4'$ and $R_5'$ is alkylammonium, and
wherein $R_8$ is H, alkyl, halo, haloalkyl or alkoxy, and, (C) a compound having the structure of Formula III

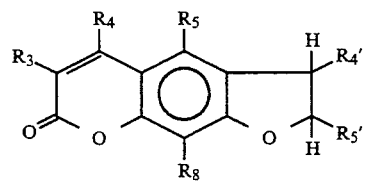

wherein $R_3$ is H, amino, alkyl or halo,
wherein $R_4$ is H, methyl or trifluoromethyl,
wherein $R_5$ is H or alkoxy,
wherein $R_4'$ and $R_5'$ are alkyl, halo or alkylammonium and at least one of $R_4'$ and $R_5'$ is alkylammonium, and
wherein $R_8$ is alkyl, halo, haloalkyl or alkoxy.

2. A photochemotherapeutic compound of the formula

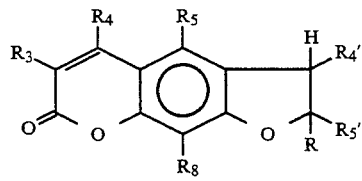

wherein $R_3$ is H, amino, nitro, carboethoxy, halo or alkyl,
wherein $R_4$ is H, methyl or trifluromethyl,
wherein $R_5$ is H or alkoxy,
wherein $R_4'$ and $R_5'$ are alkylamino or halo, and
wherein $R_8$ is H, alkyl, halo, haloakyl or alkoxy.

3. A compound of claim 2 which is 5-N-phthalimidomethyl-4',5'-dihydro-8-hydroxypsoralen.

4. A compound of claim 2 which is 5-N-phthalimidomethyl-4',5'-dihydro-8-methoxypsoralen.

5. A compound of claim 2 which is 5-amino-4',5'-dihydro-8-methoxypsoralen.

6. A compound of claim 2 which is 4,5',8-trimethyl-4'-aminomethyl-4',5'-dihydropsoralen.

7. A compound of claim 2 which is 4,4',8-trimethyl-5'-aminomethyl-4',5'-dihydropsoralen.

8. A compound of claim 2 which is 3,5-dinitro-4',5'-dihydro-8-methoxypsoralen.

9. A compound of claim 2 which is 5-iodo-4',5'-dihydro-8-methoxypsoralen.

10. A compound of claim 2 which is 3-carboethoxy-4',5'-dihydropsoralen.

11. A compound of claim 2 which is 8-methoxy-3-iodo-4',5'-dihydropsoralen.

12. A compound of claim 2 which is 8-[2-(N,N-dimethylamino)ethoxy]-4',5'-dihydropsoralen HCl salt.

13. A compound of claim 2 which is 4-trifluoromethyl-4',5'-dihydro-4',8-dimethylpsoralen.

14. A compound of claim 2 which is 4-trifluoromethyl-4',5'-dihydro-5',8-dimethylpsoralen.

15. A photochemotherapeutic compound of the formula

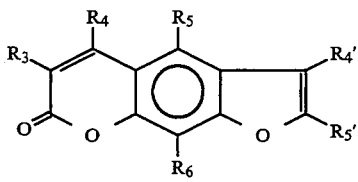

wherein $R_3$ is H, alkyl or halo,
wherein $R_4$ is H, methyl or trifluoromethyl,
wherein $R_5$ is H or alkoxy,
wherein $R_4'$ and $R_5'$ are alkylammonium, alkyl or halo, and at least one of $R_4'$ and $R_5'$ is alkylammonium, and
wherein $R_8$ is H, alkyl, halo, haloalkyl or alkoxy.

16. The compound of claim 15 which is 5'-[(N-pyridinium)methyl]-4,8-dimethylpsoralen or salts thereof.

17. The compound of claim 15 which is 4'-bromo-5'-N-[(4-ethylpyridinium)methyl]-4,8-dimethylpsoralen or salts thereof.

18. A compound of claim 15 which is 5'-bromo-4'-N-[(4-ethylpyridinium)methyl]-4,8-dimethylpsoralen or salts thereof.

19. A compound of claim 15 which is 3,5'-dibromo-4'-N-[(4-ethylpyridinium)methyl]-4,8-dimethylpsoralen or salts thereof.

20. A compound of claim 15 which is 5'-[N,N,N-trimethylammonium)methyl]-4,4',8-trimethylpsoralen or salts thereof.

21. A compound of claim 15 which is 5'-[N-(4-ethylpyridinium)methyl]-4,8-dimethylpsoralen or salts thereof.

22. A compound of claim 15 which is 5'-[N,N-dimethylammonium)methyl]-4,8-dimethylpsoralen or salts thereof.

23. A compound of claim 15 which is 5'-[N,N,N-trimethylammonium)methyl]-4,8-dimethylpsoralen or salts thereof.

24. A photochemotherapeutic compound of the formula

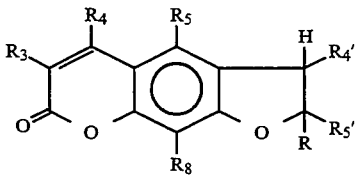

wherein $R_3$ is H, amino, alkyl or halo,
wherein $R_4$ is H, methyl or trifluoromethyl,
wherein $R_5$ is H or alkoxy,
wherein $R_4'$ and $R_5'$ are alkyl, halo or alkylammonium and at least one of $R_4'$ and $R_5'$ is alkylammonium, and
wherein $R_8$ is alkyl, halo, haloalkyl or alkoxy.

25. A compound of claim 24 which is 5'-[(N,N,N-trimethylammonium)methyl]-4',5'-dihydro-4,8-dimethylpsoralen or salts thereof.

26. A compound of claim 24 which is 5'-[(N-morpholino-N-methylammonium)methyl-4',5'-dihydro-4,8-dimethylpsoralen or salts thereof.

27. A compound of claim 24 which is 4'-bromo-5'-[(N,N,N-trimethylammonium)methyl]-4',5'-dihydro-4,8-dimethylpsoralen or salts thereof.

28. A method of treating a proliferative skin disorder in a human patient comprising administering to said patient either parenterally, orally or topically an effective amount of a compound as recited in claim 1, 2, 15 or 24 and then irradiating said patient with ultraviolet light.

29. A photochemotherapeutic formulation comprising an effective amount of compound as recited in claim 1, 2, 15 or 24 in admixture with suitable carriers, stabilizers or adjuvants.

30. A method of treating a disease of the blood or bone marrow in a human patient comprising the steps of:
first, obtaining cells from the blood or bone marrow of said patient;
second, introducing in vitro into said cells a compound as recited in claims 1 2, 15 or 24;
third, exposing said cells containing said compound to ultraviolet light; and,
fourth, returning said cells to the blood or bone marrow of said patient.

31. A method of treating a disease of the blood or bone marrow in a human patient comprising the steps of:
first, administering to said patient a compound as recited in claims 1, 2, 15 or 24;
second, obtaining cells from the blood or bone marrow of said patient;
third, exposing said cells to ultraviolet irradiation; and,
fourth, returning said cells to the blood or bone marrow of said patient.

32. A photochemotherapeutic formulation comprising an effective amount of a compound as recited in claim 1, 2, 15 or 24 in admixture with suitable carriers, stabilizers or adjuvants.

* * * * *

UNITED STATES PATENT AND TRADEMARK OFFICE
CERTIFICATE OF CORRECTION

PATENT NO. : 5,356,929
DATED : October 18, 1994
INVENTOR(S) : Ned D. Heindel and Jeffrey D. Laskin It is certified that error appears in the above-indentified patent and that said Letters Patent is hereby corrected as shown below:

Page 2, "Other Publications" section,

Column 1, line 19, delete "Mamographs" and insert therefor --Monographs";

lines 24 and 25, delete "American Chemical Society" and insert therefor --J. Org. Chem.--;

line 29, delete "Jouranl" and insert therefor --Journal--;

and

Column 2, lines 27, delete "Transfer Hydrogenations of Furocoumarin Derivatives[1]" by N. Heindel et al.; Biochemistry, 1983, vol. 48, pp. 3817-3818".

Column 1, line 12, insert

--This invention was made with government support under NIH Agreement ES 03467. The government has certain rights in this invention.--

Signed and Sealed this

Twenty-first Day of February, 1995

Attest:

BRUCE LEHMAN

Attesting Officer     Commissioner of Patents and Trademarks